United States Patent [19]

Giordano et al.

[11] Patent Number: 4,748,253

[45] Date of Patent: * May 31, 1988

[54] PROCESS FOR PREPARING ESTERS OF ALKANOIC ACIDS VIA REARRANGEMENT OF ALPHA-HALOKETALS

[75] Inventors: Claudio Giordano, Monza; Aldo Belli, Novara; Fulvio Uggeri, Codogno; Giovanni Villa, Monticello Brianza, all of Italy

[73] Assignee: Blasinachim S.p.A., Milan, Italy

[*] Notice: The portion of the term of this patent subsequent to Nov. 8, 2000 has been disclaimed.

[21] Appl. No.: 329,333

[22] Filed: Dec. 10, 1981

Related U.S. Application Data

[62] Division of Ser. No. 236,524, Feb. 20, 1981, abandoned.

[30] Foreign Application Priority Data

Feb. 26, 1980 [IT] Italy ............................... 20187 A/80
Aug. 7, 1980 [IT] Italy ............................... 24045 A/80

[51] Int. Cl.$^4$ ..................... C07D 333/24; C07C 69/76
[52] U.S. Cl. ....................................... 549/79; 560/100; 560/102; 560/109; 560/111

[58] Field of Search ................. 549/79; 560/100, 102, 560/109, 111

[56] References Cited

FOREIGN PATENT DOCUMENTS 1535690 12/1978 United Kingdom .

OTHER PUBLICATIONS

Olah, "Friedel–Crafts & Related React.", vol. 1 (1963), pp. 254–255.

*Primary Examiner*—Alan Siegel
*Attorney, Agent, or Firm*—Stevens, Davis, Miller & Mosher

[57] ABSTRACT

Process for preparing esters of alkanoic acids via rearrangement of alpha-haloketals in the presence of a Lewis acid.

The rection is preferably carried out in the presence of catalytic amounts of a Lewis acid and of a diluent at a temperature in the range from about 0° to the reflux temperature of diluent.

The esters thus obtained are useful as intermediate products for preparing drugs.

The process involves the preparation of new alpha-haloketals.

2 Claims, No Drawings

PROCESS FOR PREPARING ESTERS OF ALKANOIC ACIDS VIA REARRANGEMENT OF ALPHA-HALOKETALS

This is a division of application Ser. No. 236,524, filed Feb. 20, 1981, now abandoned.

This invention relates to a new process for preparing esters of alkanoic acids via rearrangement of alpha-haloketals in the presence of a Lewis acid.

More particularly, the new process of this invention is represented by the following scheme:

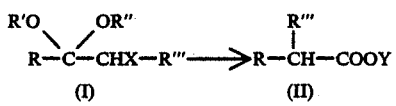

wherein

R is selected from the group comprising an aryl, a substituted aryl, a fused heterocyclic aryl, an heterocyclic a substituted heterocyclic and a fused aryl-heterocyclic radical;

R' is selected from the group comprising an alkyl radical having from 1 to 6 carbon atoms and a benzyl radical;

R" is selected from the group comprising an alkyl radical having from 1 to 6 carbon atoms and a benzyl radical;

R' and R", together, are an alkylene radical having from 2 to 6 carbon atoms which, together with the

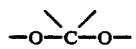

group, forms a heterocyclic ring;

X is a halogen atom;

R''' is selected from the group comprising a hydrogen atom, an alkyl having from 1 to 6 carbon atom, an aryl, a substituted aryl, a fused heterocyclic-aryl, an heterocyclic, a substituted heterocyclic, a fused arylheterocyclic radical;

Y is selected from the group comprising an alkyl radial having from 1 to 6 carbon atoms, a halo-alkyl radical having from 2 to 6 carbon atoms and a benzyl radical.

The esters of general formula II may be hydrolized by conventional procedures to afford the corresponding alkanoic acids which are useful as such or as intermediate products; many of them are useful as drugs. More particularly many members of this class are known to be useful as anti-inflammatory, analgesic and antipyretic agents; examples of such compounds include ibuprofen, fenclorac, indoprofen, flurbiprofen, naproxen, ketoprofen, fenoprofen, piroprofen, suprofen, aclofenac, xenbucin, diclofenac and tolmetin (Anti-Inflammatory Drugs, Springer Verlag, 1979, pages 321-3).

Other members of this class, such as thienyl acetic acid, are useful as intermediate products for preparing semisynthetic penicillins and cephalosporins or for preparing anti-inflammatory drugs such as thiaprofenic acid.

The most part of the known synthetic routes for preparing alpha aryl-alkanoic acids involves the substitution of the aromatic ring with an acyl radical because this substitution may be carried out in high yields and with a high positional selectivity. The subsequent step is consisting in the transformation of the acyl moiety into the alkanoic moiety via Darzen reaction, via a variation of Wittig reaction which comprises the use of methoxycarbenylides instead of carbenylides, via Grignard reaction, via cyanidrine or via reduction to alcohol, subsequent halogenation and treatment with a cyanide or carbon monoxide.

All of the above mentioned procedures present many drawbacks because they involve many steps, the yields are usually low and the reagents are expensive and highly polluting.

In consideration of what above, many efforts have been made to prepare aryl-alkanoic acids via rearrangement of the acyl-derivatives.

A known oxidative rearrangement is the Willgerodt reaction, but it is of industrial value only for preparing arylacetic acids from arylmethyl-ketones and it does not allow to achieve good yields because of the many purifications that are needed for eliminating the sulfur-containing by-products.

British Pat. No. 1.535.690 describes a process which comprises (i) the acylation of an aromatic hydrocarbon (ii) the reaction of the ketone thus obtained to prepare the corresponding ketal (iii) the generation of an enol ether from the corresponding ketal (iv) the rearrangement of the enol ether with thallium ions in an organic liquid containing, per equivalent of the enol ether at least one equivalent of a nucleophilic compound. This process suffers the disadvantage that thallium can react with the aromatic moiety to form some by-products.

The alkanoic acids, prepare according to this synthetic route, contain always traces of thallium as metal and/or as metal-organic product and are potentially dangerous because of the very high toxycity of thallium.

Surprisingly, it has been now found that Lewis acids (J. March—Advanced Organic Chemistry, Mc Graw-Hill and Kogakusha e., 2 edt., 236-8; Chem. Rev., 75, No. 1, 1-20) act as catalysts in preparing esters of formula II via rearrangement pathway of ketals of formula I.

In order to obtain the rearrangement, the process is carried out in such a way that the catalyst exerts a good affinity toward the halogen atom and a poor affinity toward the oxygen atom of the ketal group in the alpha-halo-ketal (I).

Meantime, it must be avoided such a condition that catalyst acts as a reducing agent and transforms alpha-halo-hetals (I) into ketals and/or ketones.

Catalyst that ma be used according to this invention are the organic salts, such as acetate, propionate, benzoate, trifluoromethane sulphonate, methane sulphonate, etc. as well a the inorganic salts such as chloride, bromide, iodide, sulphate etc. of Copper, Magnesium, Calcium, Zinc, Cadmium, Barium, Mercury, Tin, Antimony, Bismuth, Manganese, Iron, Cobalt, Nickel and Palladium.

A preferred embodiment of this invention contemplates the use of metal halides such as $ZnCl_2$, $CoCl_2$, $ZnBr_2$, $SnCl_2$, $FeCl_2$, $FeCl_3$, $NiBr_2$, $CdCl_2$, $MgCl_2$, $HgCl_2$, $Hg_2Cl_2$, $SbCl_3$, $BaCl_2$, $CaCl_2$, $CuCl$, $CuCl_2$, $MnCl_2$, $SnCl_4$, $BiCl_3$, $PdCl_2$.

The catalyst may be introduced directly into the reaction medium; alternatively, it is formed "in situ".

The catalyst is preferably used in catalytic amount; larger quantities do not afford apreciable advantages.

The rearrangement according to this invention is preferably carried out in the presence of a suitable diluent. Examples of such diluents are the aliphatic halohydrocarbons, aliphatic cyclic-hydrocarbons, lower alcohols, aliphatic acids and their esters, aromatic hydrocarbons and halo aromatic hydrocarbons such as dichloroethane, trichloroethane, chlorobenzene, toluene, methylene chloride, methanol, trimethyl orthoformate, and their mixtures.

The rearrangement contemplated by this invention is conducted at a temperature in the range from about 0° C. to the reflux temperature of the diluent.

Considering that either ketals (I) or esters (II) are stable at high temperature, a preferred embodiment of this invention contemplates the use of high boiling diluents.

The reaction time differs according to the ketal reactivity, the catalyst activity and the reaction temperature; so it is very wide and it is comprised in the range from about ½ hour to about 160 hours.

The meaning of Y in the general formula II is related to the nature of the ketal and/or the diluent.

When R' and R" are alkyl radicals or benzyl radicals and the diluent is not a nucleophilic compound, Y has the same meaning of R' and R".

When an alcohol is used as diluent it may also take part in the esterification and/or transesterification step by forming esters of general formula II wherein Y is the alkyl radical of the alcohol used as diluent. When an alkylene-alpha-halo-ketal (I) is rearranged, then Y (in the ester II) may be an halo-alkyl-radical because the halogen atom (X in formula I) replaces one oxygen atom of the starting ketal.

Furthermore, scrambling between the anion of the metal salt and the halogen-atom (X in formula I) may take place during the rearrangement step so that the anion of the metal salt may be present as substituent instead of X in the radical Y.

The halo-ketals (I) are prepared in an easy way and in high yields from the corresponding ketons either (i) by halogenation of the ketone and subsequent ketalization of the thus obtained alpha-halo-ketone or (ii) by ketalization of the ketone and subsequent halogenation of the thus obtained ketal.

The ketalization step may be carried out according to conventional procedures by means of an alcohol in the presence of an acid catalyst and of an ortho ester. When the ketal is prepared from a glycol, the water which is formed during the reaction is usually removed by azeotropic distillation for example with benzene, toluene, xylene, tetrachloroethane.

The introduction of the halogen-atom in alpha position of carbonyl group or of ketal group may be carried out by means of conventional reagents such as sulfuryl chloride, cupric chloride, cupric bromide, N-bromosuccinamide, pyridine or pyrrolidone-perbromide hydrobromide.

The halogenation step, the ketalization step and the rearrangement of alpha-halo-ketals of general formula I can be carried out in the same reaction vessel without isolating any intermediate product and in the presence of the same diluent.

The ketones that are used as starting materials according to this invention may be prepared according to the Friedel-Crafts reaction.

The ketals of general formula I wherein
R''' is an alkyl radical;
R is a substituted aryl, a fused heterocyclic-aryl, an heterocyclic, a substituted heterocyclic and a fused aryl-heterocyclic radical;
R', R" and X have the above mentioned meaning, are new and, therefor, they are a further object of this invention.

Examples of such compounds include:
2-bromo-1,1-dimethoxy-1-(6'-methoxy-2'-naphtyl)-propane
-2-chloro-1,1-dimethoxy-1-(6'-methoxy-2'-naphtyl)-propane
-2-bromo-1,1-diethoxy-1-(6'-methoxy-2'-naphtyl)-propane
-2-(1'-bromoethyl)-2-(6'-methoxy-2'-naphtyl)-1,3-dioxolane
-2-(1'-bromoethyl)-2-(6'-methoxy-2'-naphtyl)-1,3-dioxane
-2-(1'-bromoethyl)-2-(6'-methoxy-2'-naphtyl)-4,5-dimethyl-1,3-dioxolane
-2-(1'-bromo-ethyl)-2-(5'-bromo-6'-methoxy-2'-naphtyl)-1,3-dioxolane
-2-(1'-bromoethyl)-2-(4'-isobutyl-phenyl)-1,3-dioxolane
-2-(1'-chloro-ethyl)-2-(4'-isobutyl-phenyl)-1,3-dioxolane
-2-(1'-bromoethyl)-2-(4'-isobutyl-phenyl)-1,3-dioxane
-2-(1'-bromoethyl)-2-(4'-isobutyl-phenyl)-4,5-dimethyl-1,3-dioxolane
-2-bromo-1-(4'-isobutyl-phenyl)-1,1-dimethoxy-propane
-2-(1'-bromoethyl)-2-(4'-propionamido-phenyl)-1,3-dioxolane
-2-(1'-bromoethyl)-2-(4'-phthalimido-phenyl)-1,3-dioxolane
-2-(1'-bromoethyl)-2-(2-fluoro-4-diphenylyl)-1,3-dioxolane
-2-bromo-1,1-dimethoxy-1-(2'-thienyl)-propane
-2-(1'-bromo-propyl)-2-(4-diphenylyl)-1,3-dioxolane The following specific description is given to enable those skilled in this art to more clearly understand and practice the present invention. It should not be considered as a limitation upon the scope of the invention but merely as being illustrative and representative thereof.

For all the examples I.R. spectra have been recorded in nujol/NaCl; whereas N.M.R. spectra have bene recorded with a 60 MHz spectrometer. The chemical shifts have been expressed in delta [ppm].

EXAMPLE 1

(a) 2-bromo-1,1-dimethoxy-1-(6'-methoxy-2'-naphtyl)-propane (A)

A mixture of 2-bromo-1-(6'-methoxy-2'-naphtyl)-propan-1-one (257 g, 0.877 mol) (prepared according to Bull. Soc. Chim. Fr., 1962, 90), trimethyl orthoformate (271.5 g, 2.56 mol), methanesulfonic acid (1.7 g) and of methanol (700 ml) is kept, under stirring, at 45° C. for 24 h. The reaction mixture is poured, under vigorous stirring, into a saturated sodium carbonate solution and extracted with ethyl ether (2×500 ml).

The combined organic extract is washed with a 2% sodium hydrogen carbonate solution.

Evaporation of the solvent is vacuo leaves 2-bromo-1,1-dimethoxy-1-(6'-methoxy-2'-naphtyl)-propane (290 g, 0.855 mol; yield: 97.5%).

An analytically pure sample is prepared by crystallization from methanol/trimethyl orthoformate mixture; m.p. 87°–89° C.

I.R.: C=O stretching is absent. No band is present in the 2.5–3.2 microns region.

N.M.R.: (CDCl$_3$/TMS): 1.53 (d, 3H, J=7 Hz); 3.26 (s, 3H); 3.43 (s, 3H); 3.90 (s, 3H); 4.50 (q, 1H, J=7 Hz); 7–7.98 (m, 6H).

(b) 2-chloro-1,1-dimethoxy-1-(6'-methoxy-2'-naphtyl)-propane (B)

A mixture of CuCl$_2$·2H$_2$O (24.56 g, 0.144 mol), lithium chloride (3.06 g, 0.072 mol), 1-(6'-methoxy-2'-naphtyl)-propan-1-one (12.9 g, 0.060 mol) (prepared according to J. Chem. Soc. (C), 1966, 181) and of DMF (40 ml) is kept, under stirring, at 80° C. for 5 h. The solution is poured into a 3% hydrochloric acid, extracted with ethylether (2×100 ml). The combined organic extract is washed with water, dried on Na$_2$SO$_4$ and the solvent is removed in vacuo. The residue is crystallized from ethanol to give the chloroketone (10.1 g, 0.41 mol; yield: 68%) as analytically pure product, m.p. 76°–78° C.

I.R.: 1680 cm$^{-1}$ (C═O stretching). N.M.R.: (CDCl$_3$/TMS): 1.72 (d, 3H, J=7 Hz); 3.84 (s, 3H); 5.35 (q, 1H, J=7 Hz); 6.9–8.5 (m, 6H).

A mixture of 2-chloro-1-(6'-methoxy-2'-naphtyl)-propan-1-one (6 g, 24.1 mmol), trimethyl orthoformate (8 g, 75.4 mmol), methanesulfonic acid (0.5 ml, 7.7 mmol) and of methanol (18 ml) is heated at reflux for 30 h. The reaction mixture is cooled to room temperature. The white solid, which precipitates, is collected by filtration, washed with a mixture of trimethyl orthoformate and methanol and dried; 5.35 g, 18 mmol, yield: 75%; m.p. 92°–94° C.

I.R.: C═O stretching is absent. No band is present in the 2.5–3.2 microns region.

N.M.R.: (CH$_2$Cl$_2$/TMS): 1.42 (d, 3H, J=7 Hz); 3.3 (s, 3H); 3.45 (s, 3H); 3.95 (s, 3H); 6.85–8.35 (m, 6H).

(c) 2-bromo-1,1-diethoxy-1-(6'-methoxy-2'-naphtyl)-propane (C)

A solution of 2-bromo-1,1-dimethoxy-1-(6'-methoxy-2'-naphthyl)-propane (obtained according to Example 1a) (3.39 g, 10 mmol), triethyl orthoformate (1.34 g, 9 mmol) and of methanesulfonic acid (0.098 g, 1 mmol) in ethanol (30 ml) is kept at 46° C. for 2 h.

The reaction mixture is poured, under vigorous stirring, into a saturated sodium carbonate solution and extracted with ethyl ether (2×250 ml). The combined organic extract is washed with a 2% sodium hydrogen carbonate solution and dried on Na$_2$CO$_3$. Evaporation of the solvent in vacuo leaves 2-bromo-1,1-diethoxy-1-(6'-methoxy-2'-naphtyl)-propane (3.67 g, 10 mmol, yield: 100%) as oil.

I.R.: C═O stretching is absent. No band is present in the 2.5–3.2 microns region.

N.M.R.: (CCl$_4$/TMS): 1.23 (t, 6H, J=7 Hz); 1.53 (d, 3H, J=7 Hz); 3.43 (q, 4H, J=7Hz); 3.90 (s, 3H); 4.50 (q, 1H, J=7 Hz); 7.00–8.00 (m, 6H).

(d) 2-(1'-bromoethyl)-2-(6'-methoxy-2'-naphtyl)-1,3-dioxolane (D)

A mixture of 2-bromo-1,1-dimethoxy-1-(6'-methoxy-2'-naphtyl)propane (1 g, 2.94 mmol) (obtained according to Example 1a), trimethyl orthoformate (0.5 ml, 4.7 mmol), BF$_3$·Et$_2$O (0.3 ml), and of ethylene glycol (10 ml, 179.5 mmol) is kept at 50° C. for 3 h. It is cooled to room temperature and poured, under vigorous stirring, into a saturated sodium carbonate solution and extracted with ethyl ether (2×250 ml).

The combined organic extract is washed with a 2% sodium hydrogen carbonate solution.

Evaporation of the solvent in vacuo leaves 2-(1'-bromoethyl)-2-(6'-methoxy-2'-naphtyl)-1,3-dioxolane (0.97 g, 2.88 mmol), yield: 98%).

An analytically pure product is obtained by crystallization from methanol, m.p. 75° C.

I.R.: C═O stretching is absent. No band is present in the 2.5–3.2 microns region.

N.M.R.: (CDCl$_3$/TMS): 1.60 (d, 3H, J=7 Hz); 3.90 (s, 3H); 3.90 (m, 2H); 4.13 (m, 2H); 4.48 (q, 1H, J=7 Hz); 7.04–7.92 (m, 6H).

(e) 2-(1'-bromoethyl)-2-(6'-methoxy-2'-naphtyl)-1,3-dioxane (E)

2-bromo-1-(6'-methoxy-2'-naphtyl)-propan-1-one (10 g, 34 mmol), 1,3-propandiol (10.5 g, 138 mmol), para-toluenesulfonic acid hydrate (1g, 5.3 mmol) and benzene (50 ml) are refluxed and stirred together for 1 h in a flask beneath a Dean-Stark trap.

The reaction mixture is added dropwise to a well stirred saturated sodium carbonate solution (100 ml), extracted with benzene (2×100 ml). The combined organic solution is washed with a 2% sodium hydrogen carbonate solution, dried (Na$_2$CO$_3$), filtered and concentrated in vacuo to give 2-(1'-bromoethyl)-2-(6'-methoxy-2'-naphtyl)-1,3-dioxane (11.9 g, 34 mmol, yield: 100%) as oil.

I.R.: C═O stretching is absent. No band is present in the 2.5–3.2 microns region.

N.M.R.: (CH$_2$Cl$_2$/TMS): 1.20 (m, 2H); 1.68 (d, 3H, J=7Hz); 3.90 (m, 4H); 3.96 (s, 3H); 4.30 (q, 1H, J=7 Hz); 7.12–7.98 (m, 6H).

(f) 2-(1'-bromoethyl)-2-(6'-methoxy-2'-naphtyl)-4,5-dimethyl-1,3-dioxolane (F)

The preparation is carried out according to the method described in Example 1e.

Reagents: (±)-2,3-butanediol (10 g, 111 mmol), 2-bromo-1-(6'-methoxy-2'-naphtyl)-propan-1-one (10 g, 34 mmol).

Catalyst: para-toluenesulfonic acid hydrate (1 g, 5.25 mmol)

Solvent: benzene (50 ml)

Reaction time: 7 h

Yield: 12.3 g, 33.7 mmol, 99%, as oil

I.R.: C═O stretching is absent. No band in the 2.5–3.2 microns region.

N.M.R.: (CDCl$_3$/TMS): 1.23 (m, 6H); 1.53 (broad d, 3H, J=7 Hz); 3.65 (m, 2H); 3.83 (s, 3H); 4.43 (q, 1H, J=7 Hz); 7.00–8.00 (m, 6H).

(g) 2-(1'-bromo-ethyl)-2-(5'-bromo-6'-methoxy-2'-naphtyl)-1,3-dioxolane (G)

Bromine (7.9 g, 100 mmol) is added, in 30 minutes, to a stirred solution of 2-bromo-1-(6'-methoxy-2'-naphtyl)-propan-1-one (29.3 g, 100 mmol) in chloroform (200 ml), kept at room temperature.

The precipitate is filtered and heated at reflux with methanol.

The heterogeneous mixture is cooled to room temperature, the insoluble is filtered, washed with methanol and dried: 2-bromo-1-(5'-bromo-6'-methoxy-2'-naphtyl)-propan-1-one (24 g, 64.3 mmol;
yield: 64%); m.p. 168°–170° C.

I.R.: 1680 cm$^{-1}$ (C═O stretching)

N.M.R.: (CDCl$_3$/TMS): 1.95 (d, 3H, J=7 Hz); 4.08 (s, 3H); 5.43 (q, 1H, J=7 Hz); 7.23–8.60 (m, 5H).

The 2-bromo-1-(5'-bromo-6'-methoxy-2'-naphtyl)-propan-1-one is converted into 2-(1'-bromoethyl)-2-(5'-bromo-6'-methoxy-2'-naphtyl)-1,3-dioxolane according to the method described in example 1e.

Reagents: ethylene glycol (33.3 g, 0.54 mol), 2-bromo-1-(5'-bromo-6'-methoxy-2'-naphtyl)-propan-1-one (20 g, 0.054 mol)

Catalyst: para-toluenesulfonic acid hydrate (1 g, 5.3 mmol)

Solvent: toluene (25 ml)

Reaction time: 8 h

Yield: 22.1 g, 53 mmol, 99%; m.p. 103°–104° C. (methanol)

I.R.: C=O stretching is absent. No band is present in the 2.5–3.2 microns region.

N.M.R.: (CDCl$_3$/TMS): 1.60 (d, 3H, J=7Hz); 4.00 (m, 2H): 4.03 (s, 3H): 4.16 (m, 2H); 4.46 (q, 1H, J=7 Hz); 7.20–8.36 (m, 5H).

(h) 2-(1'-bromoethyl)-2-(4'-isobutyl-phenyl)-1,3-dioxolane (H) 2-bromo-1-(4'-isobutyl-phenyl)-propan-1-one (67.5 g, 0.250 mol), ethylene glycol (78 g, 1.26 mol), para-toluenesulfonic acid hydrate (2.4 g, 12.6 mmol) and toluene (80 ml) are heated and stirred together for 5 h in a flask beneath a Dean-Stark trap. The reaction mixture is added dropwise to a well stirred saturated sodium carbonate solution (1 l) and extracted with toluene (2×100 ml).

The combined organic solution is washed with a 2% sodium hydrogen carbonate solution, dried (Na$_2$CO$_3$), filtered and concentrated in vacuo to give the desired ketal as oil (77.3 g, 0.247 mol; yield 99%).

I.R.: C=O stretching is absent; no band is present in the 2.5–3.2 microns region.

N.M.R. (CCl$_4$/TMS): 0.89 (d, 6H, J=6 Hz); 1.48 (d, 3H, J=7 Hz); 1.85 (m, 1H, J=6 Hz); 2.43 (d, 2H, J=6 Hz); 2.43 (d, 2H, J=6 Hz); 4.00 (m, 5H); 6.9–7.9 (AA'BB', 4H).

(i) 2-(1'-chloro-ethyl)-2-(4'-isobutyl-phenyl)-1,3-dioxolane (I)

A solution of CuCl$_2$ (13.5 g, 100 mmol), LiCl (3.2 g, 76 mmol), 4'-isobutyl-propiophenone (9.33 g, 49 mmol) in DMF (40 ml) is kept at 83° C. for 3 h.

The solution is poured into a 3% hydrochloric acid, extracted with toluene. The organic extract is washed with water and the solvent is removed in vacuo. The residue is crystallized from methanol to give the desired chloroketone (6.35 g, 28.3 mmol, yield 58%) as analytically pure product, m.p. 53.5°–54.5° C.

I.R.: C=O stretching 5.95 microns

N.M.R.: (CCl$_4$/TMS) 0.89 (d, 6H, J=7 Hz); 1.75 (d, 3H, J=7 Hz); 2.53 (d, 2H, J=7Hz); 5.20 (q, 1H, J=7 Hz); 7.1–8.1 (AA'BB', 1H).

Following the procedure of Example 1e the ketal T is prepared

Reagents: 2-chloro-4'-isobutyl-propiophenone (26 g, 116 mmol) above prepared, ethylene glycol (36 g, 0.58 mol).

Catalyst: para-toluenesulfonic acid hydrate (1.1 g, 5.78 mmol).

Solvent: Toluene (40 ml)

Reaction time: 4 h

Yield: 29.6 g, 110 mmol, 95% as oil

I.R.: C=O stretching is absent; no band is present in the 2.5–3.2 microns region.

N.M.R: (CCl$_4$/TMS): 0.89 (d, 6H, J=6 Hz); 1.30 (d, 3H, J=7 Hz); 1.82 (h, 1H, J=6Hz); 2.41 (d, 2H, J=6 Hz); 3.89 (m, 5H); 6.9–7.4 (AA'BB', 4H).

(j) 2-(1'-bromoethyl)-2-(4'-isobutyl-phenyl)-1,3-dioxane (J)

Is prepared according to the procedure of Example 1e Reagents: 2-bromo-1-(4'-isobutyl-phenyl)-propan-1-one (13.5 g, 50 mmol); 1,3 propanediol (19 g, 250 mmol).

Catalyst: para-toluenesulfonic acid hydrate (0.5 g, 2.6 mmol)

Solvent: Toluene (50 ml)

Reaction time: 16 h

Yield: 16.05 g, (49 mmol; 98%) as oil

I.R.: C=O stretching is absent; no band is present in the 2.5–3.2 microns region N.M.R.: CCl$_4$/TMS): 0.89 (d, 6H, J=6 Hz); 1.43 (d, 3H, J=7 Hz); 1.1–2.3 (m, 3H); 2.42 (d, 2H, J=6 Hz); 3.75 (m, 5H); 6.9–7.4 (AA'BB', 4H).

(k) 2-(1'-bromoethyl)-2-(4'isobutyl-phenyl)-4,5-dimethyl-1,3-dioxolane (K)

Is prepared according to the procedure of Example 1e.

Reagents: 2-bromo-1-(4'-isobutyl-phenyl)-propan-1-one (13.5 g, 50 mmol); 2,3-butanediol (112.5 g, 1.25 mol).

Catalyst: para-toluenesulfonic acid hydrate (0.5 g, 2.6 mmol)

Solvent: Toluene (50 ml)

Reaction time: 14 h

Yield: (17.05 g, 50 mmol, 100%) as oil

I.R.: C=O stretching is absent; no band is present in the 2.5–3.2 microns region.

N.M.R. (CCl$_4$/TMS): 0.89 (d, 6H, J=6 Hz); 1.1–2.3 (m, 10H), 2.40 (d, 2H, J=6 Hz); 4.06 (m, 3H); 6.9–7.4 (AA'BB', 4H)

(l) 2-bromo-1-(4'-isobutyl-phenyl)-1,1-dimethoxy-propane (L)

Bromine (160 g, 1 mol) is added dropwise to a well stirred solution of 4'-isobutyl-propiophenone (190 g, 1 mol) in chloroform (500 ml), kept at 15° C.

The solution is stirred for additional 2 h. It is poured into water and the organic layer is washed with water and with a saturated sodium hydrogen carbonate solution.

It is dried (Na$_2$SO$_4$), filtered and concentrated in vacuo to give 2-bromo-4'-isobutyl-propiophenone (263 g, 0.98 mol, yield 98%).

An analytically pure sample is prepared by crystallization from methanol: m.p. 65°–67° C.

I.R.: C=O stretching 5.26 microns

N.M.R. (CCl$_4$/TMS): 0.89 (d, 6H, J=6 Hz), 1.85 (m, 4H); 2.53 (d, 2H, J=7 Hz); 5.17 (q, 1H, J=6 Hz); 7.1–8.1 (AA'BB', 4H).

A solution of 2-bromo-4'-isobutyl-propiophenone (5.4 g, 20 mmol), thus obtained, trimethyl orthoformate (6.54 g, 62 mmol), methanesulfonic acid (0.4 ml) and of methanol (65 ml) is kept at 50° C. for 24 h.

The solution is poured, under vigorous stirring, into a saturated sodium carbonate solution (0.2 l), extracted with toluene (2×150 ml).

The combined organic extract is washed with a 2% sodium hydrogen carbonate solution.

Evaporation of the solvent in vacuo leaves an oil consisting of ketal L (5.04 g, 16 mmol; yield 80%).

N.M.R. (CCl$_4$/TMS): 0.89 (d, 6H, J=6 Hz); 1.45 (d, 3H, J=7 Hz); 1.85 (m, 1H, J=6 Hz); 2.43 (d, 2H, J=6 Hz); 3.10 (s, 3H); 3.30 (s, 3H); 4.30 (q, 1H, J=7 Hz); 6.9–7.4 (AA'BB', 4H).

(m) 2-bromo-1,1-dimethoxy-1-(4'-methoxy-phenyl)-ethane (M)

A solution of 2-bromo-1-(4'-methoy-phenyl)-ethanone (22.9 g, 0.1 mol), trimethyl orthoformate (25 g, 0.236 mol), methanesulfonic acid (0.73 g, 0.0076 mol) and methanol (100 ml) is kept at 60° C. for 3 h.

The solution is poured, under vigorous stirring, into a saturated sodium carbonate solution (0.2 l), extracted with ethyl ether (3×50 ml). The combined organic extract is washed with a 2% sodium hydrogen carbonate solution. Evaporation of the solvent in vacuo leaves an oil. Crystallization of the residue from methanol gives 2-bromo-1,1-dimethoxy-1-(4'-methoxy-phenyl)-ethane (23.5 g, 0.085 mol; yield 85%) as analytically pure product. m.p. 52°–53° C.

I.R.: C≡O stretching is absent. No band is present in the 2.5–3.2 microns region.

N.M.R. (CDCl$_3$/TMS): 3.20 (s, 6H); 3.60 (s, 2H); 3.79 (s, 3H); 6.78–7.48 (AA'BB', 4H).

(n) 2-iodo-1,1-dimethoxyl-1-(4'-methoxy-phenyl)-ethane (N)

A mixture of 2-bromo-1-(4'-methoxy-phenyl)-ethanone (22.9 g, 0.1 mol), potassium iodide (66.4 g, 0.4 mol) and acetone (200 ml) is heated at reflux for 3 h. The reaction mixture is cooled, poured into water (0.25 l) and extracted with ethyl ether (3×100 ml) The combined organic extract is washed with water and dried (Na$_2$SO$_4$). Evaporation of the solvent in vacuo leaves a residue which by crystallization from petroleum ether gives 2-iodo-1-(4'-methoxy-phenyl)-ethanone (22 g, 0.094 mol, yield 80%), m.p. 63°–65° C.

A mixture of 2-iodo-1-(4'-methoxy-phenyl)-ethanone (8.3 g, 0.03 mol), trimethyl orthoformate (10 g, 0.08 mol), methanesulfonic acid (0.146 g, 0.0015 mol) and of methanol (50 ml) is kept at 60° C. for 3 h. The solution is poured, under vigorous stirring, into a saturated sodium carbonate solution (0.2 l) and extracted with ethyl ether (3×50 ml).

The combined organic extract is washed with a 2% sodium hydrogen carbonate solution.

The solvent is evaporated in vacuo; crystallization of the residue from methanol gives 2-iodo-1,1-dimethoxy-1-(4'-methoxy-phenyl)-ethane (7.5 g, 0.023 mol, yield: 77%) as analytically pure product.

m.p. 54°–55° C.

I.R.: C≡O stretching is absent. No band in the 2.5–3.2 microns region.

(o) 2-bromo-1,1-diethoxy-1-(4'-methoxy-phenyl)-ethane (O)

A solution of 2-bromo-1-(4'-methoxy-phenyl)-ethanone (5 g, 22 mmol), triethyl orthoformate (9 g, 61 mmol), methanesulfonic acid (0.3 g, 3.1 mmol) and ethanol (20 ml) is kept at 40° C. for 3 h. The solution is poured, under vigorous stirring, into a saturated sodium carbonate solution (0.2 l) and extracted with ethyl ether (3×50 ml). The combined organic extract is washed with a 2% sodium hydrogen carbonate solution. Evaporation of the solvent in vacuo leaves an oil, which is crystallized from methanol to give 2-bromo-1,1-diethoxy-1-(4'-methoxy-phenyl)-ethane (5 g, 16 mmol, yield: 73%) as analytically pure product.

m.p.: 55°–56° C.

I.R.: C≡O stretching is absent. No band in the 2.5–3.2 microns region.

N.M.R. (CCl$_4$/TMS): 1.23 (t, 6H, J=7.6 Hz); 3.47 (q, 4H, J=7.6 Hz); 3.57 (s, 2H); 3.80 (s, 3H); 6.73–7.47 (AA'BB', 4H).

(p) 2-bromomethyl-2-(4'-methoxy-phenyl)-1,3-dioxolane (P)

2-bromo-1-(4'-methoxy-phenyl)-ethanone (20 g, 87 mmol), ethylene glycol (54 g, 870 mmol), para-toluenesulfonic acid hydrate (1.7 g, 8.7 mmol) and benzene (50 ml) are heated and stirred together for 5 h in a flask beneath a Dean-Stark trap. The reaction mixture is added dropwise to a well stirred saturated sodium carbonate solution (0.4 l) and extracted with ethyl ether (3×70 ml). The combined organic extract is washed with a 2% sodium hydrogen carbonate solution, dried (Na$_2$CO$_3$) and filtered. The solvent is evaporated under reduced pressure to give 2-bromomethyl-2-(4'-methoxy-phenyl)-1,3-dioxolane (23.5 g, 86 mmol; yield: 99%).

Crystallization from methanol gives an analytically pure sample.

m.p. 78°–79° C.

I.R.: C≡O stretching is absent. No band in the 2.5–3.2 microns region.

N.M.R.: (CDCl$_3$/TMS): 3.67 (s, 2H); 3.83 (s, 3H); 3.90 (m, 2H); 4.13 (m, 2H); 6.80–7.53 (AA'BB', 4H).

(q) 2-bromomethyl-2-(4'-methoxy-phenyl)-1,3-dioxane (Q)

Is prepared according to the procedure of Example 1e.

Reagents: 2-bromo-1-(4'-methoxy-phenyl)-ethanone (10 g, 43.6 mmol); 1,3-propanediol (33 g, 434 mmol);

Catalyst: p-toluenesulfonic acid hydrate (0.85 g, 4.4 mmol)

Solvent: Toluene (25 ml)

Reaction time: 8 h

Yield: 99%

Crystallization from methanol gives an analytically pure sample.

m.p.: 80°–81° C.

I.R.: C≡O stretching is absent. No band is present in the 2.5–3.2 microns region.

N.M.R.: (CDCl$_3$/TMS): 1.20 (m, 2H); 3.40 (s, 2H); 3.86 (s, 3H); 3.88 (m, 4H); 6.86–7.47 (AA'BB', 4H).

(r) 2-bromomethyl-2-(4'-methoxy-phenyl)-4,5-dimethyl-1,3-dioxolane (R)

Is prepared according to the procedure of example 1e. Reagents: 2-bromo-1-(4'-methoxy-phenyl)-ethanone (10 g, 43.6 mmol); (±) 2,3-butanediol (40 g, 444 mmol).

Catalyst: para-toluenesulfonic acid hydrate (0.85 g, 4.4 mmol)

Solvent: benzene (25 ml)

Reaction time: 6 h

Yield: 99% (as oil)

I.R.: C≡O stretching is absent. No band in the 2.5–3.2 microns region.

N.M.R.: (CDCl$_3$/TMS): 1.03 (d, 3H, J=5.6 Hz); 1.33 (d, 3H, J=5.6 Hz); 3.60 (s, 2H), 3.80 (s, 3H); 3.92 (m, 2H); 6.12–7.22 (AA'BB', 4H).

(s) 2-(1-bromoethyl)-2-(4'-propionamido-phenyl)-1,3-dioxolane (S)

Aluminum chloride (600 g, 4.50 mol) is added in portion to a cold (0°–10° C.) stirred solution of propionanilide (230 g, 1.54 mol) and of propionyl chloride (297 g, 3.2 mol) in carbon disulphide (600 ml). The reaction mixture is heated at reflux for 24 h. It is poured into a mixture of hydrochloric acid and crushed ice, and extracted with methylene chloride. The organic phase is washed with a 1% sodium hydrogen carbonate solution, with water, dried (Na$_2$SO$_4$) and filtered. Evaporation of the solvent under reduced pressure gives 1-(4'-propionamidophenyl)-propan-1-one (165 g, 0.8 mol, yield 52%) m.p. 154°–155° C.

I.R.: 3320 cm$^{-1}$ (NH stretching); 1665, 1710 cm$^{-1}$ (C≡O stretching).

N.M.R.: (CDCl$_3$/TMS): 1.20 (t, 3H, J=7 Hz); 1.25 (t, 3H, J=7 Hz); 2.45 (q, 2H, J=7 Hz); 2.95 (q, 2H, J=7 Hz); 7.50–8.07 (AA'BB', 4H).

A solution of bromine (16 g, 0.1 mol) in acetic acid (5 ml) is added in 30 min, at room temperature, to a stirred solution of 1-(4'-propionamidophenyl)-propan-1-one (20.5 g, 0.1 mol) in acetic acid (200 ml).

The solution is poured into a 2% sodium sulphite solution and extracted with methylene chloride (2×100 ml).

The combined organic extract is washed with water, dried with Na$_2$SO$_4$. Evaporation of solvent in vacuo leaves a solid residue.

Crystallization from methanol provides 2-bromo-1-(4'-propionamido-phenyl)-propan-1-one (23 g, 0.081 mol, yield 81%) as analytically pure product, m.p. 126°–127° C.

I.R.: 1670 cm$^{-1}$ (C=O stretching), 3390 cm$^{-1}$ (NH stretching).

N.M.R.: (CDCl$_3$/TMS): 1.23 (t, 3H, J=7 Hz); 1.87 (d, 3H, J=7 Hz); 2.45 (q, 2H, J=7 Hz); 5.30 (q, 1H, J=7 Hz); 7.27–8.08 (AA'BB', 4H).

The bromoketone (7 g, 25 mmol), above prepared, ethylene glycol (20 g, 322 mmol), para-toluenesulfonic acid hydrate (0.5 g, 2.6 mmol) and toluene (20 ml) are heated at reflux and stirred together for 3 h in a flask beneath a Dean-Stark trap. The reaction mixture is added dropwise to a well stirred saturated sodium carbonate solution and extracted with methylene chloride (2×50 ml). The combined organic solution is washed with a 2% sodium hydrogen carbonate solution, dried (Na$_2$CO$_3$), filtered and concentrated in vacuo to give (7.3 g, 22.3 mmol, yield 90%) as oil.

I.R.: C=O stretching is absent.

N.M.R.: (CDCl$_3$/TMS): 1.20 (t, 3H, J=7 Hz); 1.55 (d, 3H, J=7 Hz); 2.35 (q, 2H, J=7 Hz); 4.00 (m, 4H); 4.30 (q, 1H, J=7 Hz); 7.00–7.67 (m, 4H).

(t) 2-(1'-bromoethyl)-2-(4'-phthalimido-phenyl)-1,3-dioxolane (T)

A mixture of 1-(4'-aminophenyl)-propan-1-one (30 g, 0.2 mol), phthalic anhydride (60 g, 0.4 mol) and of acetic acid (300 ml) is heated at reflux for 2 h. The reaction mixture is cooled to room temperature and the precipitate consisting of 1-(4'-phthalimidophenyl)-propan-1-one (41 g, 0.150 mol, yield 75%) is filtered and dried in vacuo An analytically pure sample is obtained by crystallization from acetic acid, m.p. 213°–214° C.

I.R.: 1660, 1640, 1680 cm$^{-1}$ (C=O stretching)

N.M.R.: (CDCl$_3$/TMS): 1.23 (t, 3H, J=7 Hz); 3.04 (q, 2H, J=7 Hz); 7.27–8.27 (m, 8H).

N,N,N,N-trimethyl-phenylammonium perbromide (37.6 g, 0.1 mol) is added, in portion, at room temperature, to a stirred solution of the ketone (28 g, 0.1 mol) (above prepared) in tetrahydrofurane (700 ml).

The reaction mixture is filtered, the insoluble washed with tetrahydrofurane. Evaporation in vacuo of the combined tetrahydrofurane solution leaves 2-bromo-1-(4'-phtalimido-phenyl)-propan-1-one (36 g, 0.1 mol, yield: 100%) as solid residue.

An analytically pure sample is prepared by crystallization from acetic acid; m.p. 189°–190° C.

I.R.: 1650 cm$^{-1}$ (C=O stretching)

N.M.R.: (CDCl$_3$/TMS): 1.90 (d, 3H, J=7 Hz); 5.34 (q, 1H, J=7 Hz); 7.35–8.35 (m, 8H).

The bromoketone (18 g, 50 mmol), above prepared, ethylene glycol (30 g, 0.48 mol) para-toluenesulfonic acid hydrate (1 g, 5.2 mmol) and toluene (35 ml) are refluxed and stirred together for 5 h in a flask beneath a Dean-Stark trap.

The reaction mixture is added dropwise to a well stirred saturated sodium carbonate solution and extracted with methylene chloride.

The combined organic solution is washed with a 2% sodium hydrogen carbonate solution, dried (Na$_2$CO$_3$), filtered and concentrated in vacuo to give the ketal as oil (17.5 g, 45 mmol, yield 90%).

I.R.: C=O stretching is absent. No band in the 2.5–3.2 microns region.

N.M.R.: (CDCl$_3$/TMS): 1.64 (d, 3H, J=7 Hz); 3.87 (m, 2H); 4.17 (m, 2H); 4.42 (q, 1H, J=7 Hz); 7.20–8.10 (m, 8H).

(u) 2-(1'-bromoethyl)-2-(2-fluoro-4-diphenylyl)-1,3-dioxolane (U)

Bromine (0.56 g, 35 mmol) is added, at room temperature and under vigorous stirring, to a solution of 1-(2-fluoro-4-diphenylyl)-propan-1-one (0.8 g, 35 mmol) (prepared according to Japan Kokai 79.109.952—Aug. 26, 1979) in chloroform (50 ml). The reaction mixture is poured, under stirring, into a sodium sulfite saturated solution and extracted with chloroform. The organic extract is washed with water, dried (Na$_2$SO$_4$) and filtered.

Evaporation of the solvent under reduced pressure gives 2-bromo-1-(2-fluoro-4-diphenylyl)-propan-1-one (1 g, 32.5 mmol, yield 93%).

N.M.R.: (CDCl$_3$/TMS): 1.85 (d, 3H, J=7 Hz); 5.20 (q, 1H, J=7 Hz); 7.50 (m, 8H).

2-bromo-1-(2-fluoro-4-diphenylyl)-propan-1-one (1 g, 32.5 mmol), ethylene glycol (27 g, 435 mmol) and para-toluenesulfonic acid hydrate (0.06 g, 3.00 mmol) and toluene (25 ml) are heated at reflux and stirred together for 5 h in a flask beneath a Dean-Stark trap. The reaction mixture is added dropwise to a well stirred saturated sodium carbonate solution and extracted with toluene.

The organic extract is washed with a 2% sodium hydrogen carbonate solution, dried (K$_2$CO$_3$) and filtered.

Evaporation of the solvent under reduced pressure gives 2-(1-bromoethyl)-2-(2-fluoro-4-diphenylyl)-1,3-dioxolane (1.06 g, 30.2 mmol, yield 93%).

N.M.R.: (Toluene/TMS): 1.60 (d, 3H, J=7 Hz); 4.35 (q, 1H, J=7 Hz).

(v) 2-bromo-1,1-dimethoxy-1-(2'-thienyl)-propane (V)

A solution of 2-bromo-1-(2'-thienyl)-propan-1-one (10.9 g, 50 mmol) [prepared according to Doklady Akad. Nausk. S.S.S.R. 138, 115 (1961)], trimethyl orthoformate (16 g, 150 mmol), methanesulfonic acid (1.4 g, 14.5 mmol) in methanol (60 ml) is kept at 45° C. for 22 h. Then it is heated at 60° C. for 2 h.

The solution is poured, under vigorous stirring, into a saturated sodium carbonate solution (0.2 l) and extracted with ethyl ether (3×70 ml). The combined organic extract is washed with a 2% sodium hydrogen carbonate solution.

Evaporation of the solvent under reduced pressure gives 2-bromo-1,1-dimethoxy-1-(2'-thienyl)-propane (9.5 g, 36 mmol, 72%) as oil.

I.R.: C=O stretching is absent. No band in the 2.5–3.2 microns region.

N.M.R.: (CDCl$_3$/TMS): 1.60 (d, 3H, J=7 Hz); 3.25 (s, 3H); 3.35 (s, 3H); 4.5 (q, 1H, J=7 Hz); 7.00–7.50 (m, 3H).

(w) 2-(1'-bromo-propyl)-2-(4-diphenylyl)-1,3-dioxolane (W)

Bromine (159.8 g, 1 mol) is added to a solution of 2-bromo-1-(4-diphenylyl)-butan-1-one (224 g, 1 mol) [prepared in accordance with J. Amer. Chem. Soc., 63, 1939 (1941)] in chloroform (1000 ml) kept at room temperature, under vigorous stirring.

The reaction mixture is poured into a saturated solution of sodium sulfite. The organic layer is washed with water, dried (Na₂SO₄) and filtered.

The solvent is evaporated under reduced pressure and the residue is crystallized from methanol to give 2-bromo-1-(4-diphenylyl)-butan-1-one (287 g, 0.95 mol; yield 95%), m.p. 73°–74° C.

N.M.R.: (CDCl₃/TMS): 1.08 (t, 3H, J=7 Hz); 2.13 (m, 2H); 5.11 (t, 1H, J=7 Hz); 7.37–8.23 (m, 9H).

I.R.: 1680 cm$^{-1}$ (C=O stretching)

The ketal W is prepared according to the procedure of Example 1e.

Reagents: 2-bromo-1-(4-diphenylyl)-butan-1-one (5 g, 16.5 mmol); ethylene glycol (25 g, 403 mmol)

Catalyst: para-toluenesulfonic acid hydrate (0.32 g, 1.68 mmol)

Solvent: Toluene (25 ml)

Reaction time: 10 h

Yield: 100%

I.R.: C=O stretching is absent. No band in the 2.5–3.2 microns region.

N.M.R.: (CDCl₃/TMS) 0.97 (t, 3H, J=7 Hz); 1.83 (m, 2H); 4.00 (m, 4H); 4.26 (t, 1H, J=7 Hz); 7.30–7.82 (m, 9H).

In a similar way the following compounds may be prepared:

2-bromo-1-(3'-chloro-4'-cyclohexyl-phenyl)-1,1-dimethoxy-ethane 2-bromomethyl-2-(3'-chloro-4'-cyclohexyl-phenyl)-1,3-dioxolane 2-bromo-1,1-dimethoxy-1-(3'-phenoxy-phenyl)-propane 2-(1'-bromo-ethyl)-2-(3'-phenoxy-phenyl)-1,3-dioxolane 2-bromo-1-(4'-bromo-phenyl)-1,1-dimethoxy-propane 2-(1'-bromo-ethyl)-2-(4'-bromo-phenyl)-1,3-dioxolane 2-(1'-bromo-ethyl)-2-[4-(1-oxo-2-iso-indolinyl)-phenyl]-1,3-dioxolane.

EXAMPLE 2 dl-2-(6'-methoxy-2'-naphtyl)-propionic acid (a) A mixture of 2-bromo-1-(6'-methoxy-2'-naphtyl)-propan-1-one (5.86 g, 20 mmol), trimethyl orthoformate (6 ml), methanesulfonic acid (0.2 ml, 3.1 mmol) and methanol (16 ml) is refluxed under stirring until the ketone is completely transformed into 2-bromo-1,1-dimethoxy-1-(6'-methoxy-2'-naphthyl)-propane.

To the solution thus obtained red cuprous oxide (1.44 g, 10 mmol) is added; the reaction mixture is refluxed under stirring for 24 h.

The suspension is cooled to room temperature and poured into water, the resulting suspension is acidified with hydrochloric acid and extracted with methylene chloride. The organic layer is separated and the solvent is removed under reduced pressure; the residue is dissolved in methanol containing 30% sodium hydroxide aqueous solution. This solution is heated at reflux for 2 h cooled to room temperature, poured into water and extracted with methylene chloride. The aqueous layer is acidified with diluted hydrochloric acid and extracted with methylene chloride.

The organic extracts are collected and dried over anhydrous sodium sulfate, then the solvent is removed under reduced pressure to give 3.95 g, of dl-2-(6'-methoxy-2'-naphthyl)-propionic acid; m.p. 158°–160° C.

Yield 86% of the theoretical amount as to the bromo-ketone used as starting product.

(b) A mixture of 2-bromo-1-(6'-methoxy-2'-naphthyl)-propan-1-one (5.86 g, 20 mmol); trimethyl orthoformate (6 ml), p-toluene-sulfonic acid hydrate (0.19 g, 1 mmol) and methanol (16 ml) is refluxed under stirring until the transformation into 2-bromo-1,1-dimethoxy-1-(6'-methoxy-2'-naphthyl)-propane is complete.

To the solution thus obtained red cuprous oxide (0.4 g, 2.8 mmol) is added; the thus obtained mixture is refluxed under stirring for 80 h.

By working up the reaction mixture according to the procedure disclosed in the Example 2a dl-2-(6'-methoxy-2'-naphthyl)-propionic acid (3.6 g) is obtained.

Yield 78% of the theoretical amount as to the bromo-ketone used as starting material.

(c) A mixture of 2-bromo-1,1-dimethoxy-1-(6'-methoxy-2'naphthyl)-propane (20 mmol), cuprous bromide (10 mmol), trimethyl orthoformate (4 ml) and methanol (16 ml) is refluxed under stirring for 160 h.

By following the procedure disclosed in the Example 2a dl-2-(6'-methoxy-2'-naphthyl)-propionic acid is obtained whereas the cuprous salt is recovered quantitatively and it is suitable for being recycled.

Yield 70% of the theoretical amount as to the bromo-ketone used as starting material.

(d) A mixture of 2-bromo-1-(6'-methoxy-2'-naphthyl)-propan-1-one (2.93 g, 10 mmol), trimethyl orthoformate (3 ml), methanesulfonic acid (0.1 ml; 1.35 mmol) and methanol (8 ml) is refluxed under stirring until the transformation into 2-bromo-1,1-dimethoxy-1-(6'-methoxy-2'-naphthyl)-propane is complete.

To the solution thus obtained cupric benzoate (3.3 g, 11 mmol) and copper powder (0.7 g, 11 mmol) are added; the thus obtained mixture is refluxed under stirring for 20 h.

By working up the reaction mixture according to the procedure disclosed in the Example 2a dl-2-(6'-methoxy-2'-naphthyl)-propionic acid (0.95 g, 4.1 mmol) is obtained.

Yield, 41% of the theoretical amount as to the bromo-ketone used as starting material.

Analogous results have been obtained by using catalytic amounts of the catalyst.

(e) A mixture of anhydrous cupric acetate (0.9 g, 5 mmol), copper powder (0.32 g, 5 mmol), methanesulfonic acid (0.7 mmol) and acetic anhydride (5 ml) is stirred for 1 h at 65° C.

To the mixture cooled to room temperature 2-bromo-1,1-dimethoxy-1-(6'-methoxy-2'-naphthyl)-propane (1.7 g, 5 mmol) is added.

The thus obtained mixture is heated to 65° C. and mantained at this temperature, under stirring for 20 h.

By working up the reaction mixture according to the procedure disclosed in the Example 2a dl-2-(6'-methoxy-2'-naphthyl)-propionic acid (0.67 g) is obtained.

Yield 58% of the theoretical amount as to the bromo-ketone used as starting material.

Analogous results have been obtained by using catalytic amounts of the catalyst.

(f) A mixture of 2-bromo-1-(6'-methoxy-2'-naphthyl)-propan-1-one (5.86 g, 20 mmol), trimethyl orthoformate (6 ml), 96% sulfuric acid (0.51 ml, 5 mmol) and of methanol (20 ml) is refluxed under stirring until the transformation into 2-bromo-1,1-dimethoxy-1-(6'-methoxy-2'-naphtyl)-propane is complete.

To the solution thus obtained red cuprous oxide (2.88 g, 20 mmol) is added; the thus obtained mixture is then refluxed under stirring for 16 h.

By working up the reaction mixture according to the procedure disclosed in the Example 2a dl-2-(6'-methoxy-2'-naphthyl)-propionic acid (3.85 g) is obtained.

Yield 84% of the theoretical amount as to the bromoketone.

Analogous results have been obtained by using catalytic amounts of the catalyst.

(g) A mixture of 2-bromo-1-(6'-methoxy-2'-naphthyl)-propan-1-one (2.93 g, 10 mmol), triethyl orthoformate (2 ml), methanesulfonic acid (0.2 ml, 2.7 mmol) and of ethanol (8 ml) is refluxed, under stirring for 48 h.

The solution of the ethyl-ketal thus obtained is cooled to 65° C. and red cuprous oxide (2.88 g, 20 mmol) is added; the reaction mixture is then kept at 65° C. under stirring for 8 h.

By working up the reaction mixture according to the procedure disclosed in the Example 2a dl-2-(6'-methoxy-2'-naphtyl)-propionic acid (0.2 g, 0.87 mmol) is obtained.

Yield 87% of the theoretical amount as to the bromoketone.

Analogous results have been obtained by using catalytic amounts of the catalyst.

(h) A mixture of copper powder (0.65 g, 10.2 mmol), methanesulfonic acid (0.04 ml, 0.6 mmol), trimethyl orthoformate (1 ml) and of methanol (4 ml) is heated at reflux, under nitrogen, for 30 min.

2-bromo-1,1-dimethoxy-1-(6'-methoxy-2'-naphtyl)-propane (1.7 g, 5 mmol) is added to the reaction mixture after cooling to room temperature.

The reaction mixture is heated at reflux for 40 h, under stirring and under nitrogen.

dl-2-(6'-methoxy-2'-naphtyl)-propionic acid (0.35 g, 1.5 mmol yield 30%) (m.p. 158°-160° C.) is isolated by working up the reaction mixture as described in Example 2a.

EXAMPLE 3

4'-methoxy-phenylacetic acid

Methanesulfonic acid (0.64 ml, 10 mmol) is added dropwise to a stirred mixture of red cuprous oxide (1.44 g, 10 mmol) and of trimethyl orthoformate (2 ml, 18 mmol) in methanol (5 ml) at room temperature. The reaction mixture is stirred at 60° for 45 min.

2-iodo-1,1-dimethoxy-1-(4'-methoxy-phenyl)-ethane (N) (1.61 g, 5 mmol) is added to the reaction mixture cooled to room temperature.

The reaction mixture is then heated to 60° C., under nitrogen, for 16 h.

4'-methoxy-phenylacetic acid (0.42 g, 2.5 mmol, yield 50%) is obtained by working up the reaction mixture as described in Example 2a.

EXAMPLE 4

Methyl ester of dl-2-(6'-methoxy-2'-naphtyl)-propionic acid

A solution is prepared by adding 2-bromo-1,1-dimethoxy-1-(6'-methoxy-2'-naphtyl)-propane (339 g, 1 mol), prepared according to the procedure disclosed in the Example 2a, to 1000 ml of methylene chloride. To this solution $ZnCl_2$ (19.8 g, 0.145 mol) is added under stirring, at 20° C.

The suspension is kept under stirring, at 20° C. for 10 h. The suspension is then washed with 10% hydrochloric acid (2×250 ml) and the solvent is removed by distillation under reduced pressure.

The yield of the methyl ester of dl-2-(6'-methoxy-2'-naphtyl)-propionic acid is 215 g, 0.88 mol, (88% of the theoretical amount).

EXAMPLE 5

2-bromoethyl-ester of dl 2-(5'-bromo-6'-methoxy-2'-naphtyl)-propionic acid

A mixture of 2-(1'-bromoethyl)-2-(5'-bromo-6'-methoxy-2'-naphtyl)-1,3-dioxolane (2 g, 4.8 mmol), $ZnBr_2$ (0.1 g, 0.45 mmol) and of toluene (5 ml) is heated at reflux for 5 h. The reaction mixture is cooled, poured into 3% hydrochloric acid (50 ml) and extracted with toluene (2×50 ml). The combined organic extract is washed with water, dried ($Na_2SO_4$) and filtered.

Evaporation of the solvent under reduced pressure gives 2-bromo-ethyl ester of 2-(5'-bromo-6'-methoxy-2'-naphtyl)-propionic acid (1.98 g, 4.75 mmol; yield 98%).

An analytically pure sample is obtained by crystallization from methanol, m.p. 78°-79° C.

I.R.: 1730 cm$^{-1}$ (C=O stretching)

N.M.R.: (CDCl$_3$/TMS): 1.57 (d, 3H, J=7 Hz); 3.40 (t, 2H, 6 Hz); 3.94 (s, 3H); 3.94 (q, 1H, 7 Hz); 4.37 (t, 2H, J=6 Hz); 7.06-8.34 (m, 5H).

EXAMPLE 6

2-bromoethyl-ester of (4'-methoxyphenyl)-acetic acid

A mixture of 2-bromomethyl-2-(4'-methoxyphenyl)-1,3-dioxolane (2.74 g, 10 mmol), $ZnBr_2$ (0.73 g, 3 mmol) and of toluene (10 ml) is heated at reflux, under stirring, for 3 h.

The reaction mixture is cooled to room temperature, poured into 3% hydrochloric acid and extracted with toluene (2×25 ml). The combined organic extract is washed with water, dried ($Na_2SO_4$) and filtered.

Evaporation of the solvent under reduced pressure gives 2-bromoethyl-ester of (4'-methoxy-phenyl)-acetic acid (2.68 g, 9.8 mmol, yield 98%) as oil.

I.R.: 1740 cm$^{-1}$ (C=O stretching)

N.M.R.: (CCl$_4$/TMS): 3.47 (t, 2H, J=6 Hz); 3.60 (s, 3H); 3.73 (s, 3H); 4.37 (t, 2H, J=6 Hz); 6.80-7.30 (AA'BB', 4H).

EXAMPLE 7

3-bromo-propyl ester of (4'-methoxy-phenyl)-acetic acid

A mixture of 2-bromomethyl-2-(4'-methoxy-phenyl)-1,3-dioxane (2.87 g, 0.01 mol), $ZnBr_2$ (1.57 g, 0.007 mol) and toluene (10 ml) is heated at reflux, under stirring, for 2 h.

The reaction mixture is cooled to room temperature, poured into 3% hydrochloric acid and extracted with toluene (2×25 ml). The combined organic extract is washed with water, dried ($Na_2SO_4$) and filtered. Evaporation of the solvent under reduced pressure gives 3-bromo-propyl ester of (4'-methoxy-phenyl)-acetic acid (2.73 g, 0.0095 mol; yield: 95%) as oil.

I.R.: 1735 cm$^{-1}$ (C=O stretching)

N.M.R. (CDCl$_3$/TMS): 2.23 (m, 2H); 3.34 (t, 2H, J=6 Hz); 3.51 (s, 2H); 3.71 (s, 3H); 4.17 (t, 2H, J=6 Hz); 6.70-7.30 (AA'BB', 4H).

In an analogous manner several alpha-halo-ketals have been rearranged in the presence of several catalysts, in several solvents and at different temperatures.

The results that have been obtained are summarized in the following table wherein:

the alpha-halo-ketals are indicated with the capital letter which follows their chemical name in Example 1;

the solvents are indicated as M (=methanol) DCE (dichloroethane, MEC (methylene chloride), TMOF (trimethyl orthoformate), TOL (toluene), TCE (tetrachloroethane), CB (chlorobenzene), p-XYL (paraxylene);

yields as to the ketal used as starting material are based on the alkanoic acids obtained via hydrolisis of crude esters.

TABLE

| Catalyst (mmol) | Ketal (mmol) | Diluent (ml) | Reaction time (h) | T (C.°) | Yield |
|---|---|---|---|---|---|
| BaCl$_2$ (1.6) | D (5) | TCE (5) | 5 | 145 | 95 |
| BaCl$_2$ (3.3) | P (10) | TCE (10) | 19 | 145 | 20 |
| BiCl$_3$ (5) | A (5) | MEC (10) | 24 | 15 | 35 |
| BiCl$_3$ (3.3) | P (10) | TOL (10) | 2 | 110 | 90 |
| BiCl$_3$ (6.3) | H (20) | TOL (40) | 21 | 110 | 79 |
| CaCl$_2$ (1.6) | D (5) | TCE (5) | 24 | 145 | 15 |
| CdCl$_2$ (1.6) | D (5) | TCE (5) | 7 | 145 | 95 |
| CoCl$_2$ (15) | A (5) | M (5) + TMOF (1) | 120 | 60 | 45 |
| CoCl$_2$ (10) | A (10) | DCE (10) | 72 | 80 | 40 |
| CoCl$_2$ (1.5) | D (4.5) | TOL (4) | 10 | 110 | 98 |
| CoCl$_2$ (3.3) | P (10) | TCE (10) | 13 | 145 | 24 |
| CoCl$_2$ (6.3) | H (20) | TOL (40) | 40 | 110 | 70 |
| CuCl$_2$ (5) | A (5) | DCE (10) | 24 | 60 | 10 |
| CuCl$_2$ (15) | A (5) | M (5) + TMOF (1) | 120 | 60 | 30 |
| CuCl$_2$ (6.3) | H (20) | TCE (40) | 21 | 145 | 63 |
| FeCl$_2$ (1.6) | D (5) | TOL (5) | 10 | 110 | 80 |
| FeCl$_2$ (3.3) | P (10) | TOL (10) | 12 | 110 | 24 |
| FeCl$_2$ (6.3) | H (20) | TOL (40) | 21 | 110 | 79 |
| FeCl$_3$ (6) | A (6) | MEC (6) | 14 | 15 | 78 |
| FeCl$_3$ (57) | A (57) | MEC (57) | 5 | 0 | 77 |
| FeCl$_3$ (3.3) | P (10) | TOL (10) | 8 | 110 | 22 |
| FeCl$_3$ (6.3) | H (20) | TOL (40) | 20 | 110 | 40 |
| Hg$_2$Cl$_2$ (1.6) | D (5) | TCE (5) | 6 | 145 | 92 |
| Hg$_2$Cl$_2$ (3.3) | P (10) | TCE (10) | 24 | 145 | 84 |
| Hg$_2$Cl$_2$ (6.3) | H (20) | TCE (40) | 8 | 145 | 75 |
| HgCl$_2$ (1.6) | D (5) | TOL (5) | 3 | 110 | 87 |
| HgCl$_2$ (3.3) | P (10) | TOL (10) | 23 | 110 | 90 |
| HgCl$_2$ (6.3) | H (20) | TCE (40) | 8 | 145 | 78 |
| MgCl$_2$ (1.6) | D (5) | TCE (5) | 22 | 145 | 35 |
| MnBr$_2$ (3.3) | P (10) | TCE (10) | 13 | 145 | 15 |
| MnCl$_2$ (15) | A (5) | M (5) + TMOF (1) | 120 | 60 | 30 |
| NiBr$_2$ (1.6) | D (5) | TCE (5) | 21 | 145 | 28 |
| NiBr$_2$ (3.3) | P (10) | TCE (10) | 13 | 145 | 13 |
| PdCl$_2$ (15) | A (5) | M (5) + TMOF (1) | 3 | 60 | 92 |
| PdCl$_2$ (0.5) | P (5) | TCE (5) | 27 | 145 | 65 |
| PdCl$_2$ (6.3) | H (20) | TCE (40) | 21 | 145 | 65 |
| SbCl$_3$ (1.6) | D (5) | TCE (5) | 3 | 145 | 96 |
| SbCl$_3$ (6.3) | H (20) | TCE (40) | 40 | 145 | 63 |
| SnCl$_2$ (1.6) | D (5) | TOL (5) | 12 | 110 | 95 |
| SnCl$_2$ (6.3) | H (20) | TCE (40) | 21 | 145 | 60 |
| SnCl$_4$ (5) | A (5) | MEC (10) | 24 | 20 | 20 |
| SnCl$_4$ (3.3) | P (10) | TOL (10) | 8 | 110 | 35 |
| SnCl$_4$ (6.3) | H (20) | TOL (40) | 21 | 110 | 77 |
| ZnBr$_2$ (3) | D (15) | TOL (30) | 4 | 110 | 98 |
| ZnBr$_2$ (1.3) | D (5) | CB (5) | 0.5 | 133 | 97 |
| ZnBr$_2$ (7) | Q (10) | TOL (10) | 2 | 110 | 90 |
| ZnBr$_2$ (1.5) | O (10) | TOL (10) | 1 | 110 | 84 |
| ZnBr$_2$ (6.3) | H (20) | TOL (40) | 21 | 110 | 73 |
| ZnBr$_2$ (3.3) | U (3.3) | TCE (25) | 2 | 145 | 54 |
| ZnBr$_2$ (7) | P (10) | TOL (10) | 3 | 110 | 98 |
| ZnBr$_2$ (21) | T (10) | p-XYL (30) | 3 | 138 | 45 |
| ZnBr$_2$ (10.5) | V (35) | TOL (50) | 0.5 | 110 | 90 |
| ZnBr$_2$ (0.40) | W (1.15) | TOL (2) | 5 | 110 | 96 |
| ZnCl$_2$ (22) | A (155) | MEC (150) | 4 | 30 | 84 |
| ZnCl$_2$ (109) | A (750) | MEC (750) | 12 | 20 | 86 |
| ZnCl$_2$ (5) | A (50) | MEC (50) | 16 | 15 | 96 |
| ZnCl$_2$ (73) | A (500) | TOL (700) | 6 | 60 | 80 |
| ZnCl$_2$ (170) | A (1000) | MEC (1000) | 10 | 20 | 88 |
| ZnCl$_2$ (11) | B (10) | MEC (15) | 8 | 45 | 43 |
| ZnCl$_2$ (2.5) | C (10) | MEC (17) | 24 | 15 | 40 |
| ZnCl$_2$ (8.4) | D (68) | TOL (200) | 6 | 110 | 96 |
| ZnCl$_2$ (3) | D (3) | MEC (6) | 24 | 15 | 10 |
| ZnCl$_2$ (3) | E (9) | TOL (10) | 16 | 90 | 90 |
| ZnCl$_2$ (4.5) | F (13.7) | TOL (15) | 14 | 90 | 80 |
| ZnCl$_2$ (7) | F (7) | MEC (20) | 24 | 45 | 30 |
| ZnCl$_2$ (1.6) | G (5) | TOL (5) | 2 | 110 | 90 |
| ZnCl$_2$ (11) | L (85) | MEC (100) | 24 | 30 | 80 |
| ZnCl$_2$ (22.6) | H (67.4) | TOL (70) | 8 | 110 | 90 |
| ZnCl$_2$ (22.6) | I (108) | TOL (100) | 7 | 110 | 94 |
| ZnCl$_2$ (19) | J (61) | TOL (50) | 17 | 110 | 81 |
| ZnCl$_2$ (19) | K (63) | TOL (50) | 40 | 110 | 70 |
| ZnCl$_2$ (3.3) | P (10) | TOL (10) | 8 | 110 | 75 |
| ZnCl$_2$ (3.3) | R (10) | TOL (10) | 6 | 110 | 81 |
| ZnCl$_2$ (5) | M (5) | MEC (10) | 24 | 40 | 30 |
| ZnCl$_2$ (15) | V (30) | MEC (30) | 5 | 24 | 60 |
| ZnCl$_2$ (7) | S (22) | TOL (40) | 6 | 110 | 40 |

TABLE-continued

| Catalyst (mmol) | Ketal (mmol) | Diluent (ml) | Reaction time (h) | T (C.°) | Yield |
|---|---|---|---|---|---|
| Zn(OAc)$_2$ (0.25) | D (5) | TOL (5) | 2 | 110 | 98 |
| Zn(OAc)$_2$ (0.25) | P (5) | TOL (5) | 8 | 110 | 98 |

We claim:

1. Process for preparing compounds having the general formula:

R—CH—COOY, wherein
R is selected from the group consisting of a phenyl, a substituted phenyl, a fused heterocyclic aryl, an heterocyclic, a substituted heterocyclic, and a fused aryl-heterocyclic radical;
R''' is selected from the group consisting of a hydrogen atom and an alkyl radical having from 1 to 6 carbon atoms;
Y is selected from the group consisting of an alkyl radical having from 1 to 6 carbon atoms, a haloalkyl radical having from 2 to 6 carbon atoms, and a benzyl radical;
which comprises the rearrangement of compounds having the general formula:

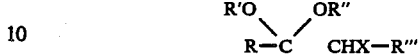

wherein
R and R''' have the above mentioned meanings, and
R' is selected from the group consisting of an alkyl radical having from 1 to 6 carbon atoms and a benzyl radical;
R'' is selected from the group consisting of an alkyl radical having from 1 to 6 carbon atoms and a benzyl radical; or
R' and R'', together, are an alkylene radical having from 2 to 6 carbon atoms which, together with the —O—C—O— group, forms an heterocyclic ring; and
X is a halogen atom;
in the presence of a Lewis acid in such an amount and under such conditions that said Lewis acid does not act toward the starting halo-ketal as either an oxidizing agent or a reducing agent.

2. Process according to claim 1 wherein the rearrangement is carried out in the presence of a catalytic amount of a Lewis acid.

* * * * *

UNITED STATES PATENT AND TRADEMARK OFFICE
CERTIFICATE OF CORRECTION

PATENT NO.  : 4,748,253
DATED       : May 31, 1988
INVENTOR(S) : GIORDANO et al.

It is certified that error appears in the above-identified patent and that said Letters Patent is hereby corrected as shown below:

On the title page assignee should read

"[73] Assignee: Blasinachim S.p.A., Milan, ITALY"

--[73] Assignee: Blaschim S.p.A.--

Signed and Sealed this

Twenty-sixth Day of September, 1989

*Attest:*

DONALD J. QUIGG

*Attesting Officer*  Commissioner of Patents and Trademarks